US009043345B2

(12) United States Patent
Davis et al.

(10) Patent No.: US 9,043,345 B2
(45) Date of Patent: May 26, 2015

(54) PUBLIC HEALTH DATA EXCHANGE BRIDGE AND POST OFFICE

(75) Inventors: Matthew A. Davis, San Jose, CA (US); James H. Kaufman, San Jose, CA (US); Sondra R. Renly, Elmsford, NY (US); John T. E. Timm, San Jose, CA (US)

(73) Assignee: International Business Machines Corporation, Armonk, NY (US)

( * ) Notice: Subject to any disclaimer, the term of this patent is extended or adjusted under 35 U.S.C. 154(b) by 128 days.

(21) Appl. No.: 13/480,835

(22) Filed: May 25, 2012

(65) Prior Publication Data

US 2013/0318111 A1 Nov. 28, 2013

(51) Int. Cl.
*G06F 17/30* (2006.01)
*G06F 7/00* (2006.01)
*G06F 19/00* (2011.01)

(52) U.S. Cl.
CPC .............. *G06F 19/32* (2013.01); *G06F 19/327* (2013.01)

(58) Field of Classification Search
USPC ................................................. 707/821, 756
See application file for complete search history.

(56) References Cited

U.S. PATENT DOCUMENTS

| 7,325,076 | B1 * | 1/2008 | Morrison et al. | ............. | 709/246 |
| 2008/0195421 | A1 * | 8/2008 | Ludwig et al. | ..................... | 705/3 |
| 2011/0225176 | A1 * | 9/2011 | Siegel et al. | .................. | 707/756 |

FOREIGN PATENT DOCUMENTS

WO 2005004027 1/2005

OTHER PUBLICATIONS

Maldonado et al. "Concept-Based Exchange of Healthcare Information: The LinkEHR Approach" Proceedings of the 2011 IEEE First International Conference on Healthcare Informatics, Imaging and Systems Biology, (2011), pp. 150-157.
Husni et al. "Telemedicine System Based on Delay Tolerant Network Delay Tolerant Network" International Conference on Electrical Engineering and Informatics (ICEEI), 2011, (Jul. 2011), 5 pages.
Rubin et al. "Bridging the Gap: Linking a Legacy Hospital Information System With a Filmless Radiology Picture Archiving and Communications System Within a Nonhomogeneous Environment" Journal of Digital Imaging, vol. 12, Supplement 1, (1999), pp. 96-98.
"Systems and Methods for Medical Information Exchange for Underwriting Insurance Policies" ip.com, IPCOM000167022D, (Jan. 29, 2008), 13 pages.
"Online Marketplace for Buyers and Sellers of Personal Medical Data" ip.com, IPCOM000141621D, (Oct. 10, 2006), 3 pages.
"A XML-based Approach to Sticky Policy Enforcement in Smarter Healthcare Environments" ip.com, IPCOM000201862D, (Nov. 29, 2010), 6 pages.

* cited by examiner

Primary Examiner — Kuen Lu
(74) Attorney, Agent, or Firm — Jeffrey T. Holman

(57) ABSTRACT

A system facilitates management of public health data. The system includes an input interface, a policy data structure, a notification compliance engine, and a data translator. The input interface receives input data content descriptive of a public health event. The policy data structure stores reporting conditions for a plurality of public health jurisdictions. The notification compliance engine reviews at least some of the reporting conditions of the policy data structure and identifies a relevant reporting condition for the input data content. The data translator derives and arranges output data content based on the input data content according to the relevant reporting condition identified by the notification compliance engine.

25 Claims, 5 Drawing Sheets

PUBLIC HEALTH DATA EXCHANGE BRIDGE AND POST OFFICE

BACKGROUND

Public health programs are tasked with the collection of individual and population data from a variety of sources. Some examples of such data include, but are not limited to, birth records, immunization records, reportable diseases, laboratory reportable findings, syndromic surveillance feeds, and death records. This data may be used to identify, investigate, perform care coordination, evaluate care outcomes, and mitigate barriers to health.

In the US, the responsibilities of public health programs, as well as their data sources, are legislated at the state level. Consequently, there can be great variation from state to state (and even county to county within a state). Typically, public health programs are subject to voluntary or mandatory reporting requirements. In both cases, the programs are consistently limited by a lack of timely reports and significant under reporting. This level of performance may be due, in part, to the lack of incentives for compliance and/or the infrequency of consequences for non-compliance.

Becoming compliant can be very challenging. There is not a universal public health reporting implementation because each public health jurisdiction can have its own policies and report receiving capabilities. This non-uniformity among public health requirements in various jurisdictions significantly increases costs for compliance.

For the majority of data sources, conventional reporting involves manual completion of a public health paper form that is mailed or faxed to the appropriate program. A few states have created web portals for smaller reporting sources to enter their data. Unfortunately, there are potential problems with implementations that rely on current paper forms and web portals. One potential problem results from manually identifying the reportable activity, reportable locality, and the locality's policies. Another potential problem involves storing the forms or maintaining web links for accessing the forms. Another potential problem involves entering the data that may exist electronically in one format into another format corresponding to a program's proprietary system. These conventional implementations also can consume a lot of time and/or resources.

In some instances, larger reporting organizations have implemented custom electronic feeds. Unfortunately, there are also potential problems with custom electronic feeds. In some implementations, there is not enough public funding to maintain these interfaces. Also, a custom electronic feed may be limited in the ability to help the reporting needs of the majority of data sources. Also, a custom electronic feed likely will not cover the cases that need reporting to jurisdictions outside the state or local jurisdiction.

SUMMARY

Embodiments of a system are described. In one embodiment, the system facilitates management of public health data. An embodiment of the system includes an input interface, a policy data structure, a notification compliance engine, and a data translator. The input interface receives input data content descriptive of a public health event. The policy data structure stores reporting conditions for a plurality of public health jurisdictions. The notification compliance engine reviews at least some of the reporting conditions of the policy data structure and identifies a relevant reporting condition for the input data content. The data translator derives and arranges output data content based on the input data content according to the relevant reporting condition identified by the notification compliance engine. Other embodiments of the system are also described.

Embodiments of a method are also described. In one embodiment, the method is a method for managing public health data. An embodiment of the method includes receiving input data content in any of a plurality of data input formats. The input data content is descriptive of a public health event. The method also includes generating standardized data content based on at least some of the input data content. The method also includes accessing a policy repository. The policy repository stores a plurality of reporting conditions for a plurality of public health jurisdictions. The method also includes identifying a relevant reporting condition for a target public health jurisdiction. The method also includes generating output data content based on the standardized data content according to the relevant reporting condition for the target public health jurisdiction. Other embodiments of the method are also described.

Embodiments of a computer program product are also described. In one embodiment, the computer program product includes a computer useable storage medium to store a computer readable program for managing public health data. When the computer readable program is executed on a computer, the computer readable program causes the computer to perform operations for managing public health data. The operations may include any of the operations described in conjunction with the methods and systems described herein.

Other aspects and advantages of embodiments of the present invention will become apparent from the following detailed description, taken in conjunction with the accompanying drawings, illustrated by way of example of the principles of the invention.

BRIEF DESCRIPTION OF THE DRAWINGS

Throughout the description, similar reference numbers may be used to identify similar elements.

DETAILED DESCRIPTION

Figure 1:
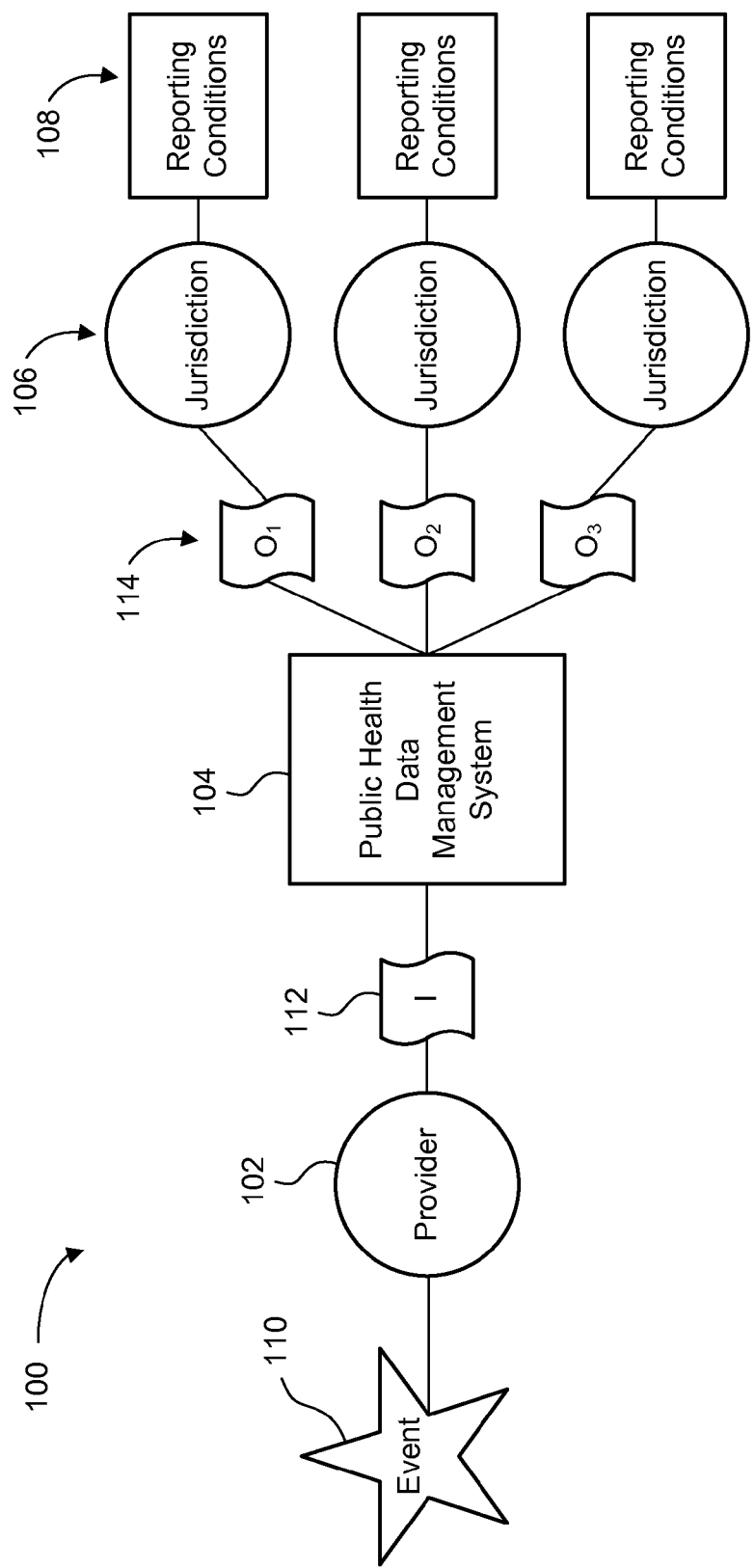
FIG. 1 depicts a schematic diagram of one embodiment of a public health data reporting environment.

It will be readily understood that the components of the embodiments as generally described herein and illustrated in the appended figures could be arranged and designed in a wide variety of different configurations. Thus, the following more detailed description of various embodiments, as represented in the figures, is not intended to limit the scope of the present disclosure, but is merely representative of various embodiments. While the various aspects of the embodiments are presented in drawings, the drawings are not necessarily drawn to scale unless specifically indicated.

The present invention may be embodied in other specific forms without departing from its spirit or essential characteristics. The described embodiments are to be considered in all respects only as illustrative and not restrictive. The scope of the invention is, therefore, indicated by the appended claims rather than by this detailed description. All changes which come within the meaning and range of equivalency of the claims are to be embraced within their scope.

Reference throughout this specification to features, advantages, or similar language does not imply that all of the features and advantages that may be realized with the present invention should be or are in any single embodiment of the invention. Rather, language referring to the features and advantages is understood to mean that a specific feature, advantage, or characteristic described in connection with an embodiment is included in at least one embodiment of the present invention. Thus, discussions of the features and advantages, and similar language, throughout this specification may, but do not necessarily, refer to the same embodiment.

Furthermore, the described features, advantages, and characteristics of the invention may be combined in any suitable manner in one or more embodiments. One skilled in the relevant art will recognize, in light of the description herein, that the invention can be practiced without one or more of the specific features or advantages of a particular embodiment. In other instances, additional features and advantages may be recognized in certain embodiments that may not be present in all embodiments of the invention.

Reference throughout this specification to "one embodiment," "an embodiment," or similar language means that a particular feature, structure, or characteristic described in connection with the indicated embodiment is included in at least one embodiment of the present invention. Thus, the phrases "in one embodiment," "in an embodiment," and similar language throughout this specification may, but do not necessarily, all refer to the same embodiment.

While many embodiments are described herein, at least some of the described embodiments implement a public health bridge and post office system.

For reference, the phrase "health care providers" is used herein to refer to any individual or entity which provides health care services to a patient. The health care providers may provide health care services directly or indirectly to a patient. Direct health care providers may include doctors and other personnel or entities which personally interact with patients. Indirect health care providers may include laboratory technicians and other personnel or entities which provide services on behalf of patients, but do not necessarily interact personally with the patients. For convenience, the health care providers also may be referred to as health care service providers, service providers, providers, or another similar designation.

To comply with notifiable condition statutes, regulations, and rules, health care providers report information about observed conditions to public health agencies in various jurisdictions. These statutes, regulations, and rules can be very specific and exist at nearly every level of government—municipal, county, state, national (e.g., U.S. Centers for Disease Control (CDC) and Prevention), and international (e.g., World Health Organization (WHO)). For example, a specific observed condition (e.g., malarial symptoms) may be reported to a specific department (e.g., tropical diseases) of multiple agencies (where the patient acquired the disease and the patient's home location). These departments may expect the information in different formats (e.g., paper form, electronic report) and delivered via different mechanisms (e.g., fax, web service). It can be difficult for a provider to know exactly where and how to report such information.

In some embodiments, the system is referred to as a "bridge" because certain functionality facilitates communicating report information from service providers to public health jurisdictions, thereby bridging the communication channel between these entities. In some embodiments, the system is also referred to as a "post office" because certain functionality facilitates storage of the report information, similar to a "post office" mail box, for subsequent retrieval by personnel from a public health jurisdiction (or another authorized user).

In one embodiment, the public health bridge and post office is a software system that provides a set of services that facilitate the collection, routing, and delivery of public health data from providers to local, state, and/or federal public health agencies. In contrast to proprietary or customized public health management systems, embodiments of the public health bridge and post office may be open community environments to support collaboration and cooperation among various entities that are otherwise unrelated.

Because different public health organizations, agencies, and jurisdictions often have different reporting requirements, the public health bridge and post office can act as a clearinghouse for such reporting requirements. The public health bridge and post office can also act as an intermediary facilitator to more accurately enable providers to send the correct information to the relevant jurisdictions according to each jurisdictions distinct content, protocol, and delivery mechanism requirements.

For example, although two different jurisdictions both may accept electronic reports, each jurisdiction may have distinct requirements on the type of electronic document format that is accepted. Similarly, each jurisdiction may have distinct requirements on the type of electronic transmission protocol that is used for the submissions. Also, each jurisdiction may have distinct requirements on the type of delivery mechanism (e.g., fax, email, etc.) that is required for the submissions.

In other examples, some jurisdictions currently may not have the necessary infrastructure or budget to implement electronic reporting. Such jurisdictions may have separate paper reporting requirements.

While several embodiments are described herein, at least some embodiments of the public health bridge may provide an open source technology that plays the role of a "post office" for reportable disease. Implemented as a service, any clinic or other provider can access the bridge to submit information on cases of reportable disease. In some embodiments, the "bridge" automatically detects other potentially relevant data based on the zip code (or other identifying characteristic) of the patients and/or the physicians. Some examples of potentially relevant data include, but are not limited to, a list of reportable conditions with medical codes by location, a supported mechanism/transmission protocol/data format of reporting (e.g., fax, Health Level 7 (HL7) Version 2 and Version 3 Messages and HL7 Clinical Document Architecture (CDA), etc.) for the local public health agency, and extensible collections of report forms customizable by local authorities. Internally the forms may be mapped to a clinical document format such as CDA. In other embodiments, other types of clinical messaging and/or clinical document formats/standards may be used. The bridge can transform and output these to any of several supported reporting standards.

In one embodiment, the most universal type of client interface to this service is an internet browser. The browser interface allows the clinician or lab to complete the appropriate structured form for the location and disease related to a particular public health event.

In some embodiments, the public health bridge also exposes an application programming interface (API) so any electronic medical records (EMR) vendor can download the technology and wrap it inside their own EMR or laboratory information management system (LIMS) application. In this way, conventional data entry steps for creating a public health report may be unnecessary. Using the API, the clinical software may populate the required form directly from the patient's record. Additionally, the system may be pluggable in that new input interfaces and delivery methods can be added without changing the core framework.

Also, by making the public health bridge available to the public health and open source communities, each local authority can contribute to and customize the forms for their location or jurisdiction. This allows each reporting jurisdiction to modify, extend, and otherwise manage as unique set of forms for reportable disease. Local authorities can also maintain a directory of where reports should be sent, as well as the metadata indicating which standard format(s) they are prepared to receive. In this way, new policies and rules also can be authored and deployed into the system.

In some embodiments, the public health bridge and post office accepts data from providers in a variety of formats. The system then converts and internally maintains the input data in a standard representation such as the standard CDA representation. This can guarantee that the stored information conforms to a known standard when the information is exported from the system to another location or system. In other embodiments, some or all of the data within the system is transient. In this way, the data is only stored for approximately the duration of one or more transactions related to the data. In either case, embodiments of the system are intended to maintain and comply with all relevant privacy and confidentiality laws and regulations.

There are many different possible uses for embodiments of the public health bridge and post office system. In one example, the system may be used for notifiable condition reporting. In another example, the system may be used in childhood immunization reporting. In another example, the system may be used in syndromic surveillance operations. Other embodiments may be used to manage public health data related to various other public health events and initiatives.

The following description of the accompanying figures provides several examples of components, functions, features that may be implemented in one or more embodiments of the public health bridge and post office system. In many instances, the public health bridge and post office system is referred to as a public health data management system. However, the user of a particular nomenclature for one embodiment or another does not limit the implementation of components, functions, and/or features that are described in conjunction with a different nomenclature. Accordingly, any component, feature, and/or function described herein, at any location herein or in combination with any embodiment herein, can be implemented in combination with any other component, feature, and/or function.

FIG. 1 depicts a schematic diagram of one embodiment of a public health data reporting environment 100. The illustrated 100 includes a health service provider 102, a public health data management system 104, and multiple reporting jurisdictions 106. The health service provider 102 and the jurisdictions 106 represent entities that are involved in the public health data reporting environment 100. As explained generally above, and in more detail below, the public health data management system 104 provides intermediary functionality to improve the convenience and accuracy of data communications from the health service provider 102 to the separate public health reporting jurisdictions 106. Although the public health data reporting environment 100 is shown and described with certain entities, components, and functionality, other embodiments of the public health data reporting environment 100 may include fewer or more entities, components, and/or functionality.

The health service provider 102 may be representative of a doctor, clinic, laboratory, or any other entity that is involved with the provision of health services. Alternatively, the health service provider 102 may be another entity that is legally, contractually, or otherwise obligated or allowed to provide reporting information to the public health reporting jurisdictions 106.

The public health reporting jurisdiction 106 is representative of any authoritative body that requires or otherwise accepts public health reports from the health service provider 102. In the United States of America, it is common to have reporting authorities at local, state, and federal levels of the government. Each of these entities may be represented by a different public health reporting jurisdiction 106.

Additionally, each of these jurisdictions 106 may have a unique set of reporting conditions 108 that specify what data is to be reported, when it should be reported, and how it should be reported. At least some of these reporting conditions 108 may specify what the report receiving capabilities are for the corresponding jurisdiction 106.

In one embodiment, the provider 102 is aware of a public health event 110 to be reported to one or more of the jurisdictions 106. The public health event 110 may be any event for which one or more of the jurisdictions 106 requires reporting. Some examples of public health events 110 that may be reported include, but are not limited to, notifiable reporting conditions, childhood immunization reporting, and syndromic surveillance activities.

The provider 102 may or may not have some type of internal system for reporting the public health event 110 to the jurisdictions 106. In either case, the provider 102 sends input data content 112 to the public health data management system 104. The input data content 112 includes subject matter descriptive of the public health event 110. The amount and type of subject matter that is included in the input data content 112 may vary, depending on the type of public health event 110. Similarly, the manner in which the input data content 112 is delivered from the provider 102 to the public health data management system 104 may vary. In some embodiment, the public health data management system includes functionality to accept various amount and types of data across various protocols and platforms.

Many of the specific functions of the public health data management system 104 are described in more detail below with reference to FIG. 2. In general, the public health data management system 104 receives the input data content 112 from the provider 102, determines which public health reporting jurisdictions 106 should receive corresponding reporting information, formats the reporting information accordingly, and sends output data content 114 to each of the jurisdictions 106.

Figure 2:
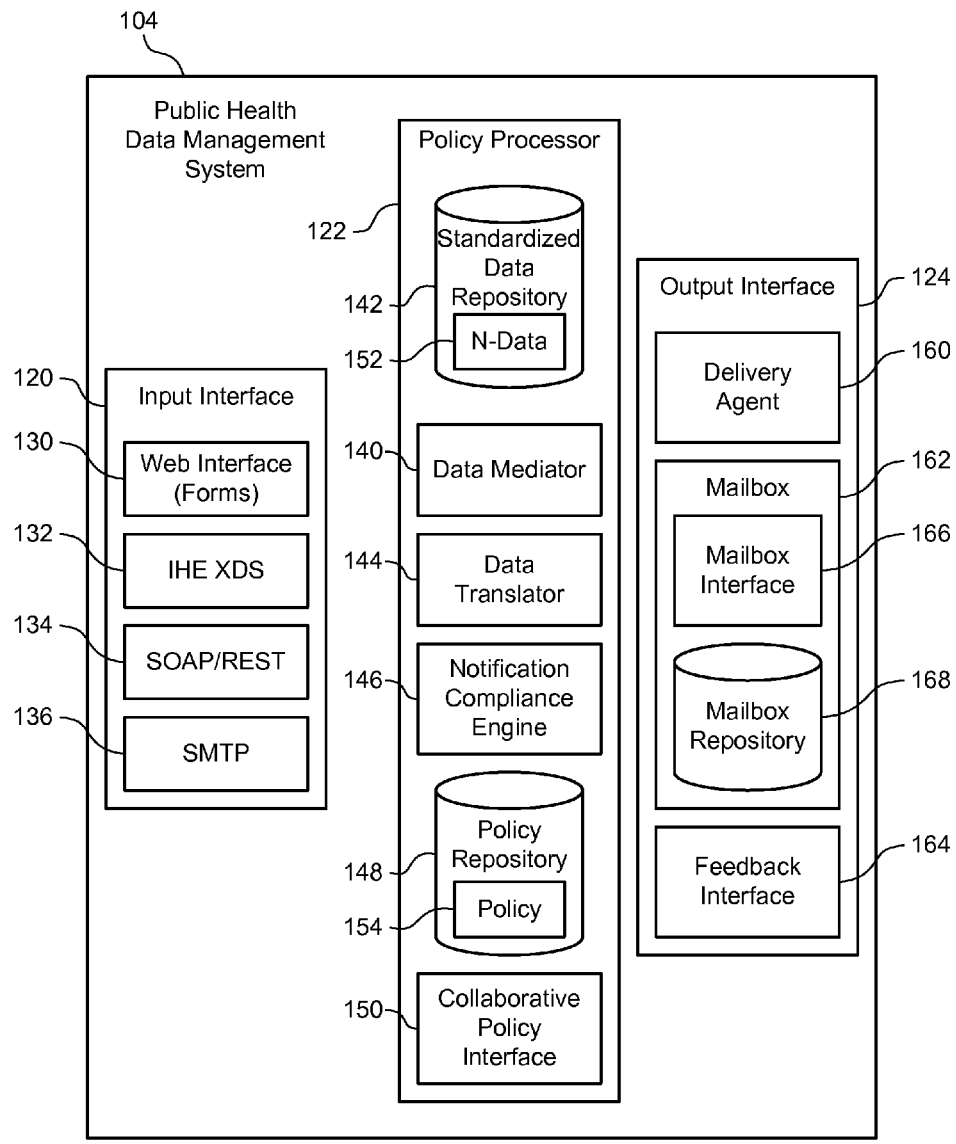
FIG. 2 depicts a schematic diagram of one embodiment of the public health data management system of FIG. 1.

FIG. 2 depicts a schematic diagram of one embodiment of the public health data management system 104 of FIG. 1. To orchestrate the transmission of documents and data between providers and/or public health agencies, the public health data management system 104 includes several logical and functional components. The illustrated public health data management system 104 includes an input interface 120, a policy processor 122, and an output interface 124. Each of these components includes further sub-components described in more detail below. Although the public health data management system 104 is shown and described with certain components and functionality, other embodiments of the public health data management system 104 may include fewer or more components to implement less or more functionality. For example, the public health data management system 104 includes communication components such as networking circuitry to facilitate electronic communications with the provider 102 and the several jurisdictions 106.

In general, the input interface 120 receives the input data content 112 from the provider 102. The policy processor 122 determines which public health reporting jurisdictions 106 should receive corresponding reporting information. The policy processor 122 also formats the reporting information for the separate reporting jurisdictions 106. The output interface 124 sends the output data content 114 to each of the jurisdictions 106.

Input Interface

When a provider 102 has a document or other patient information for delivery to the relevant public health jurisdictions 106, the provider 102 submits the document or other patient information as input data content 112 to the public health data management system 104. The provider 102 may use a clinical EMR or EHR system to submit the document/information to a standards-based interface, such as IHE Cross-Enterprise Document Sharing (XDS). The input interface also provides a forms-based web user interface (UI) to populate records for a provider who does not have a clinical EMR.

In the illustrated embodiment, the input interface 120 includes a web interface 130, an IHE XDS (e.g., NHIN Connect) interface 132, a SOAP/REST interface 134, and a SMTP (e.g., NHIN Direct) interface 136. These various interfaces facilitate receiving various types of data formats based on various types of data transmission protocols. Other embodiments may include other types of interfaces or additional interfaces for other types of data formats/protocols. In further embodiments, another standardized set of input interfaces, protocols, and schemas may be used to collect the input data content 112 from providers 102.

In one embodiment, the input interface 120 is extensible/pluggable. Data is submitted to the extensible/pluggable input interface 120. In this way, the input interface 120 may be designed to accept data over various transport protocols including, but not limited to, HTTP, SMTP, etc. and in various data interchange formats such as SOAP, proprietary XML, REST, etc.

Optionally, a provider 102 may submit data using a forms-based web UI, which is represented as the web interface 130. In one embodiment, the web interface 130 is a backstop for providers 102 that do not have other means of submitting data electronically (such as an EMR system that supports standards-based interoperability protocols). The web interface 130 may be accessed through a web browser. In one embodiment, the web interface 130 prompts the provider 102 for relevant information such as the provider's location, the type of information being reported, etc. Using this a priori knowledge, the input interface 120 may coordinate with the policy processor 122 to identify and obtain relevant forms, generate an HTML version of the proper forms, and present the HTML version to the provider 102. The provider then may populate and submit the information via the form provided via the web interface 130.

In a further embodiment, a provider 102 may utilize a combination of the various interfaces within the input interface 120 to submit the input data content 112 related to a public health event 110. As one example, the provider 102 may submit partial information via the IHE XDS interface 132. Then, upon detection (by the policy processor 122) of a requirement for further information from the provider 102, a form may be generated and presented to the provider 102 via the web interface 130 in order to obtain the additional reporting information. Other embodiments may utilize a combination of interfaces in another manner.

Policy Processor

Once the input data content 112 is submitted via the input interface 120, the input data content 112 is passed to the policy processor 122 for further manipulation. The illustrated policy processor 122 includes a data mediator 140, a standardized data repository 142, a data translator 144, a notification compliance engine 146, a policy repository 148, and a collaborative policy interface 150.

Data Mediator

The input data content 112 supplied into the public health data management system 104 can come from various sources (e.g., providers 102) and may be largely disparate. For example, some of the input data content 112 may include non-standard document formats and terminologies. To properly process this data in later stages of the pipeline, the input data content 112 is mediated and transformed (i.e., standardized) to a common, internal data model. The data mediator 140 may be pluggable and designed to support specific document formats, including standard formats such as the Continuity of Care Document (CCD), and other non-standard or proprietary inputs. The data mediator 140 generates standardized data content (N-Data) 152 that is stored in the standardized data repository 142. For example, the data mediator 140 may convert the supported input formats to a common internal data format such as a standardized XML document like HL7 CDA. In this way, the standardized data content 152 conforms to a common internal data model that can be used in further processing operations.

Notification Compliance Engine

In one embodiment, the notification compliance engine 146 provides functionality to determine which jurisdictions 106 should receive reporting information for a particular public health event 110. Also, the notification compliance engine 146 determines what reporting conditions are applicable to the identified jurisdictions 106. To comply with notifiable condition statutes, providers 102 report specific conditions to specific agencies in the correct formats using the correct protocols. In one embodiment, the notification compliance engine 146 gives the care provider 102 the public health program (i.e., jurisdiction 106) that should be notified and a mechanism for reporting. The mechanism for reporting may be the program's manual instructions for reporting, an embedded electronic report submission form, the system communication layer protocols for direct electronic submissions/confirmations, or another type of reporting format or protocol.

In one embodiment, the notification compliance engine 146 queries the policy repository 148 to determine, for particular input data content 112 submitted, to which department in which agency the reporting information should be delivered, and how it should delivered. In other words, the notification compliance engine 146 determines the destination for the public health data based on a database of destinations and a set of rules or policies.

Policy Repository

In one embodiment, the policy repository 148 aggregates the various public health statutes and policies into a database. This database may be used by the notification compliance engine 146 and the other components of the policy processor 122 to define, mediate, generate, and deliver documents to the correct public health agencies based on information submitted.

Figure 3:
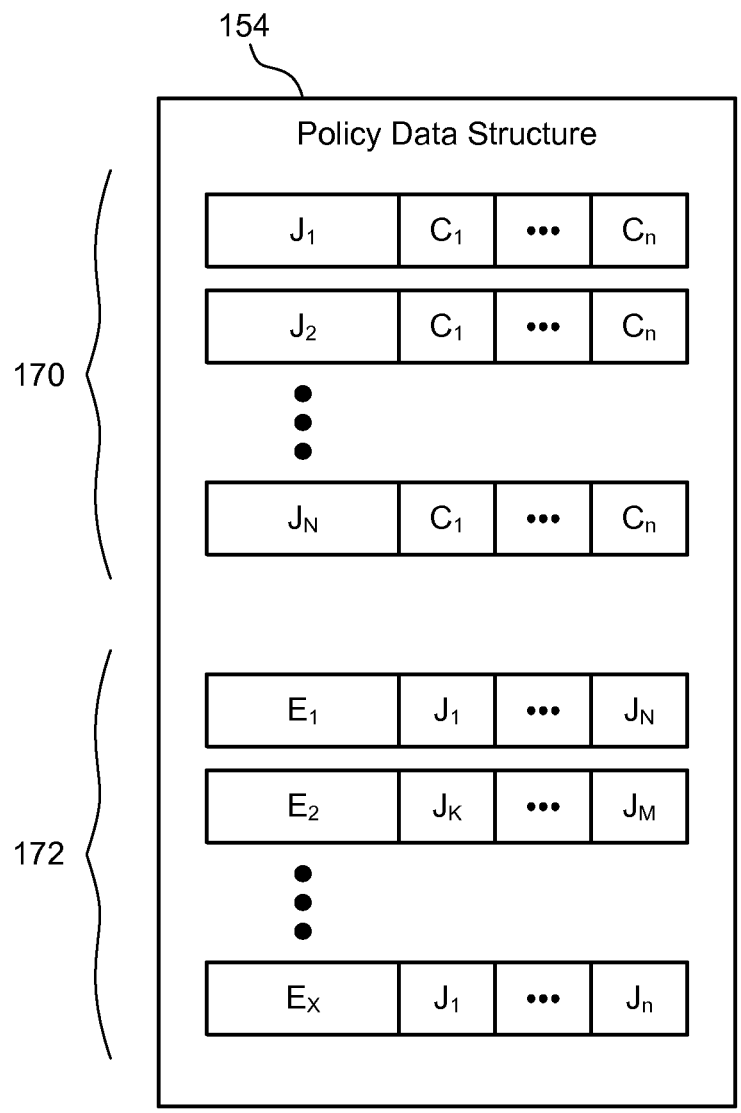
FIG. 3 depicts a schematic diagram of one embodiment of the policy data structure of FIG. 2.

The policy repository 148 includes a policy data structure 154. FIG. 3 depicts a schematic diagram of one embodiment of the policy data structure 154 of FIG. 2. The illustrated policy data structure 154 includes a plurality of entries 170 which identify reporting conditions (C) for various public health reporting jurisdictions (J) 106. The policy data structure 154 also includes entries 172 which identify jurisdictions (J) 106 that should receive reporting information for specific types of public health events (E) 110.

Although various designations and subscripts are used in the illustration of FIG. 3, such designations and subscripts are not indicative of a particular quantity or type of reporting conditions, jurisdictions 106, and/or public health events 110. Also, such designations and subscripts are not indicative of a relative quantity, order, or other characteristic among the various reporting conditions, jurisdictions 106, and/or public health events 110. Rather, each entry 170 and 172 may be customized to a particular type of reporting condition, jurisdiction 106, and/or public health event 110. Additionally, other embodiments of the policy data structure 154 may include more or less information. Also, other embodiments of the policy data structure 154 may implement other suitable arrangements for the amount and type of data associated with the policy data structure 154. Furthermore, some embodiments may implement multiple policy data structures 154 for a distributed arrangement of the data stored therein.

In some embodiments, the reporting conditions specify a content requirement. The content requirement specifies data content that is required by a target public health jurisdiction 106.

In some embodiments, the reporting conditions specify a protocol requirement. The protocol requirement specifies a data transfer protocol required by a target public health jurisdiction 106. As examples of possible protocol requirements, the reporting conditions may specify a valid delivery or target format such as a standard clinical document format such as HL7 CDA, a standard messaging format such as HL7V2, a standard document format such as portable document format (PDF), a spreadsheet format such as Microsoft Excel, a paper format such as postal mail or facsimile, an electronic voice message, or another type of format or protocol identifier.

In some embodiments, the reporting conditions specify a form. The form specifies a plurality of content fields required by a target public health jurisdiction 106.

In some embodiments, the reporting conditions specify a delivery requirement. The delivery requirement specifies a data delivery mechanism required by a target public health jurisdiction 106. As examples of possible delivery requirements, the reporting conditions may specify a destination encoded as a phone number, a fax number, an internet protocol (IP) address, a universal resource locator (URL), a postal mailing address, or another similar destination identifier.

Collaborative Policy Interface

Returning to FIG. 2, the collaborative policy interface 150 may be used by jurisdictional personnel or other authorized users to add, delete, or update one or more of the entries of the policy repository 148. Due to the size, complexity, and update frequency of the database entries, the collaborative policy interface 150 may facilitate "crowdsourcing" the management of the entries in the policy repository 148. Crowdsourcing is a type of community-driven authorship. In one embodiment, the database and tools are open source. In a specific implementation, a web-based tool is provided to receive relevant changes regarding public health policies and statutes for various jurisdictions 106.

Although various aspects of the policy repository 148 may be updated through collaborative efforts, some examples include updating policies and directories. Some examples of the types of policies that may be updated through collaborative efforts include, but are not limited to, where to report diseases and wherein to report vaccinations. Some examples of the types of directories that may be updated through collaborative efforts include, but are not limited to, directory routing tables, directory addresses, and directory phone books.

Data Translator

After the notification compliance engine 146 determines where to send the report information and what report information to send, the data translator 144 derives and arranges the output data content 114 for each corresponding jurisdiction 106. Although a single data translator 144 is shown, other embodiments may implement more than one data translator. For example, some embodiments include a separate data translator 144 for each different type of output data content 114.

In general, the data translator 144 transforms the standardized data content from the internal common data model into the correct document format (i.e., delivery format or target document format) for delivery based on information from the notification compliance engine 146. Formats may include, but are not limited to, a HL7 CDA document, a PDF that resembles a paper form, etc.

Output Interface

Once the document is in its target format, as output data content 114, the output interface 124 makes the output data content 114 available to the appropriate jurisdiction(s) 106. The illustrated output interface 124 includes a delivery agent 160 and a mailbox 162. In some embodiments, the output interface 124 also includes a feedback interface 164.

Delivery Agent

In one embodiment, the delivery agent 160 of the output interface 124 initiates delivery of the output data content 114 to the correct destination using information from the notification compliance engine 146. Delivery agents are pluggable and may include, but are not limited to, fax, paper mail, email, web service, telephone or video conference, etc.

Mailbox

The mailbox 162 provides an alternative delivery mechanism for public health agencies that do not have other means for directly receiving documents using one of the supported delivery agents 160. The illustrated mailbox 162 includes a mailbox interface 166 and a mailbox repository 168. In one embodiment, the mailbox repository 168 is a secure, internal database that stores the output data content 114 in "mailboxes" for subsequent retrieval by agencies/departments. Officials may retrieve the output data content by accessing their "mailbox" using a mailbox interface 166 such as a secure web user interface. In this way, the mailbox 162 collects public health data that can be securely accessed via a web browser or for the purposes of reporting and analysis.

Feedback Interface

In one embodiment, the feedback interface 164 provides one or more types of feedback to the provider 102 or another user of the system 100. The feedback may relate to confirmation of receipt and processing of a submission from a provider 102. Alternatively, the feedback may include summary data that identifies other potentially relevant information to communicate to the provider 102 or other authorized user. For example, the feedback interface 164 may provide the clinical EMR system or client browser (at the provider 102) with summarized or comprehensive data so the provider 102 or end user has situational awareness of other conditions that are being reported by other clinics at the time of a particular report.

In another embodiment, some or all of the standardized data content 152 or the output data content 114 may be delivered to a data warehouse for aggregation and analysis. For example, a secondary system (not shown) may monitor documents to identify early onset, cross-jurisdiction outbreaks that may not be apparent or obvious in individual jurisdictions.

Figure 4:
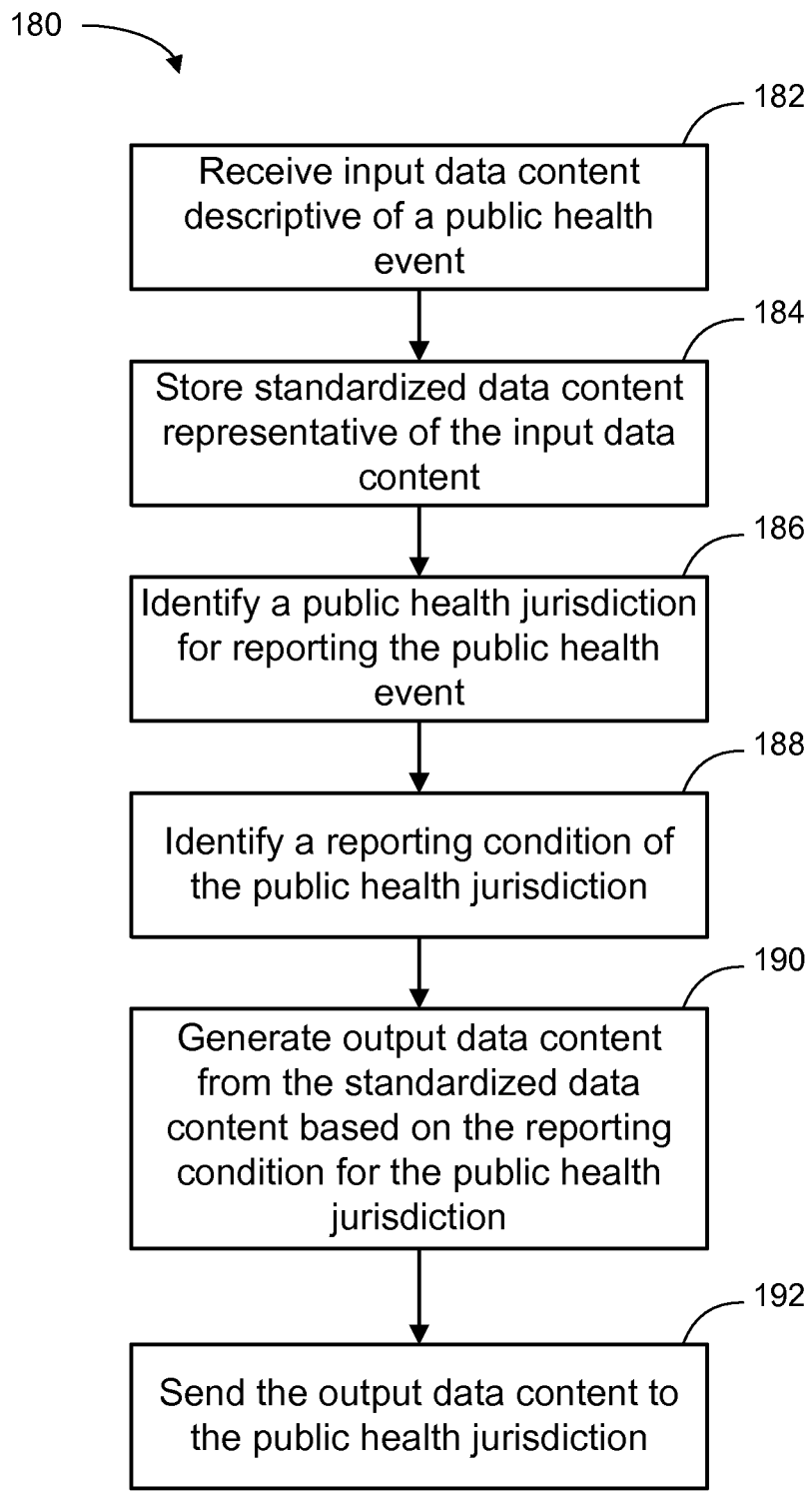
FIG. 4 depicts a flow chart diagram of one embodiment of a method for managing public health data.

FIG. 4 depicts a flow chart diagram of one embodiment of a method 180 for managing public health data. Although the method 180 is described in conjunction with the public health data management system 100 of FIG. 1, embodiments of the method 180 may be implemented with other types of data management systems.

The illustrated method begins as the input interface 120 receives 182 input data content 112 in any of a plurality of data input formats. As explained above, the input data content 112 is descriptive of a public health event 110. The data mediator 140 then generates and stores 184 standardized data content 152 in the standardized data repository 142. As mentioned above, in some cases the standardized data content 152 is only stored for a brief time period during the corresponding transaction(s) and is then deleted or otherwise removed from the system. The standardized data content 152 is representative of the input data content 112.

The notification compliance engine 146 identifies 186 a target public health jurisdiction 106 for reporting the public health event 110. The notification compliance engine 146 also identifies 188 a relevant reporting condition of the target public health jurisdiction 106. In one embodiment, the notification compliance engine 146 accesses the policy repository 148 in order to identify the target public health jurisdiction 106 and the relevant reporting condition.

The data translator 144 then generates 190 output data content 114 from the standardized data content 152 based on the relevant reporting condition for the target public health jurisdiction 106. The output interface 124 then sends 192 the output data content 114 to the target public heath jurisdiction 106. The depicted method 180 then ends.

In an alternative embodiment, the output data content 114 may be placed in the mailbox 162 for subsequent retrieval by personnel from the appropriate jurisdiction 106. In another embodiment, the output data content 114 may be sent back to the provider 102 with instructions about the preferred/required way for the provider 102 to send the output data content 114 to the appropriate jurisdiction 106. Other embodiments may include additional alternative delivery approaches.

Figure 5:
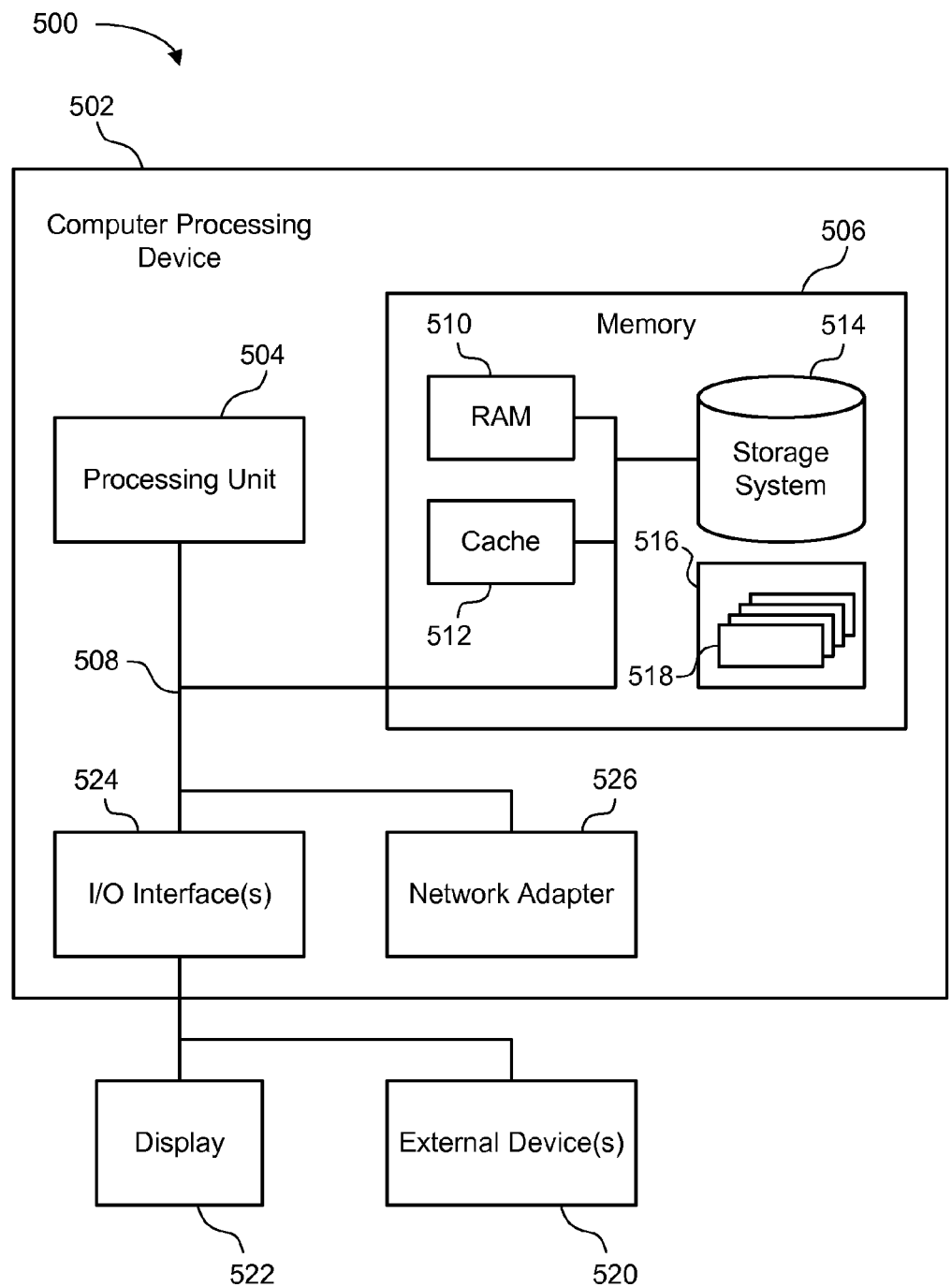
FIG. 5 depicts a schematic diagram of one embodiment of a computer system for implementation of one or more aspects of the functionality described herein.

FIG. 5 depicts a schematic diagram of one embodiment of a computer system 500 for implementation of one or more aspects of the functionality described herein. The illustrated computer system 500 is only one example of a suitable computer architecture and is not intended to suggest any limitation as to the scope of use or functionality of embodiments of the invention described herein. Regardless, the computer system 500 is capable of being implemented to performing any or all of the functionality set forth hereinabove.

The depicted computer system 500 includes a computer processing device 502, which is operational with numerous other general purpose or special purpose computing system environments or configurations. Examples of well-known computing systems, environments, and/or configurations that may be suitable for use with computer system/server 502 include, but are not limited to, personal computer systems, server computer systems, thin clients, thick clients, hand-held or laptop devices, multiprocessor systems, microprocessor-based systems, set top boxes, programmable consumer electronics, network PCs, minicomputer systems, mainframe computer systems, and distributed cloud computing environments that include any of the above systems or devices, and the like.

The computer processing device 502 may be described in the general context of computer system-executable instructions, such as program modules, being executed by a computer system. Generally, program modules may include routines, programs, objects, components, logic, data structures, and so on that perform particular tasks or implement particular abstract data types. Embodiments of the computer processing device 502 may be practiced locally, remotely, or in distributed cloud computing environments where tasks are performed by remote processing devices that are linked through a communications network. In a distributed cloud computing environment, program modules may be located in both local and remote computer system storage media including memory storage devices.

In one embodiment, the computer processing device 502 includes components and functionality typical of a general-purpose computing device. The components of the computer processing device 502 may include, but are not limited to, one or more processors or processing units 504, a system memory 506, and a bus 508 that couples various system components including the system memory 506 to the processor 504.

The bus 508 represents one or more of any of several types of bus structures, including a memory bus or memory controller, a peripheral bus, an accelerated graphics port, and a processor or local bus using any of a variety of bus architectures. By way of example, and not limitation, such architectures include Industry Standard Architecture (ISA) bus, Micro Channel Architecture (MCA) bus, Enhanced ISA (EISA) bus, Video Electronics Standards Association (VESA) local bus, and Peripheral Component Interconnect (PCI) bus.

The computer processing device 502 typically includes a variety of computer system readable media (also referred to as computer readable media and/or computer usable media). Such media may be any available media that is accessible by the computer processing device 502. Embodiments of the computer readable media may include one or more of the following types of media: volatile and non-volatile media, removable and non-removable media.

The system memory 506 can include computer system readable media in the form of volatile memory, such as random access memory (RAM) 510 and/or cache memory 512. The computer processing device 502 may further include other removable/non-removable, volatile/non-volatile computer system storage media. By way of example only, a storage system 514 can be provided for reading from and writing to a non-removable, non-volatile magnetic media (not shown and typically called a "hard drive"). Although not shown, a magnetic disk drive for reading from and writing to a removable, non-volatile magnetic disk (e.g., a "floppy disk"), and an optical disk drive for reading from or writing to a removable, non-volatile optical disk such as a CD-ROM, DVD-ROM or other optical media can be provided. In such instances, each can be connected to the bus 508 by one or more data media interfaces. As will be further depicted and described below, the memory 506 may include at least one program product having a set (e.g., at least one) of program modules that are configured to carry out the functions of embodiments of the invention.

In some embodiments, a program/utility 516, having a set (at least one) of program modules 518, is stored in the memory 506. The program modules 518 generally carry out one or more of the functions and/or methodologies of the embodiments described herein. The memory 506 also may store an operating system, one or more application programs, other program modules, and/or program data. Each of the operating system, one or more application programs, other program modules, and program data or some combination thereof, may include an implementation of a personal computer and/or networking environment.

The computer processing device 502 may also communicate with one or more external devices 520 such as a keyboard, a pointing device, a display 522, etc.; one or more devices that enable a user to interact with the computer processing device 502; and/or any devices (e.g., network card, modem, etc.) that enable the computer processing device 502 to communicate with one or more other computing devices. Such communication can occur via input/output (I/O) interfaces 524. Additionally, the computer processing device 502 can communicate with one or more networks such as a local area network (LAN), a general wide area network (WAN), and/or a public network (e.g., the Internet) via a network adapter 526. As depicted, the network adapter 526 communicates with the other components of the computer processing device 502 via the bus 508. It should be understood that, although not shown, other hardware and/or software components could be used in conjunction with embodiments of the computer processing device 502. Examples, include, but are not limited to: microcode, device drivers, redundant processing units, external disk drive arrays, RAID systems, tape drives, and data archival storage systems, etc.

Embodiments of the invention can take the form of an entirely hardware embodiment, an entirely software embodiment, or an embodiment containing both hardware and software elements. In one embodiment, the invention is implemented in software, which includes but is not limited to firmware, resident software, microcode, etc.

An embodiment of the system described herein can include at least one processor coupled directly or indirectly to memory elements through a system bus such as a data, address, and/or control bus. The memory elements can include local memory employed during actual execution of the program code, bulk storage, and cache memories which provide temporary storage of at least some program code in order to reduce the number of times code must be retrieved from bulk storage during execution.

As will be appreciated by one skilled in the art, aspects of the present invention may be embodied as a system, method or computer program product. Accordingly, aspects of the present invention may take the form of an entirely hardware embodiment, an entirely software embodiment (including firmware, resident software, micro-code, etc.) or an embodiment combining software and hardware aspects that may all generally be referred to herein as a "circuit," "module" or "system." Furthermore, aspects of the present invention may take the form of a computer program product embodied in one or more computer readable medium(s) having computer readable program code embodied thereon.

Any combination of one or more computer readable medium(s) may be utilized. The computer readable medium may be a computer readable signal medium or a computer readable storage medium. A computer readable storage medium may be, for example, but not limited to, an electronic, magnetic, optical, electromagnetic, infrared, or semiconductor system, apparatus, or device, or any suitable combination of the foregoing. More specific examples (a non-exhaustive list) of the computer readable storage medium would include the following: an electrical connection having one or more wires, a portable computer diskette, a hard disk, a random access memory (RAM), a read-only memory (ROM), an erasable programmable read-only memory (EPROM or Flash memory), an optical fiber, a portable compact disc read-only memory (CD-ROM), an optical storage device, a magnetic storage device, or any suitable combination of the foregoing. In the context of this document, a computer readable storage medium may be any tangible medium that can contain, or store a program for use by or in connection with an instruction execution system, apparatus, or device.

A computer readable signal medium may include a propagated data signal with computer readable program code embodied therein, for example, in baseband or as part of a carrier wave. Such a propagated signal may take any of a variety of forms, including, but not limited to, electro-magnetic, optical, or any suitable combination thereof. A computer readable signal medium may be any computer readable medium that is not a computer readable storage medium and that can communicate, propagate, or transport a program for use by or in connection with an instruction execution system, apparatus, or device.

Program code embodied on a computer readable medium may be transmitted using any appropriate medium, including but not limited to wireless, wireline, optical fiber cable, RF, etc., or any suitable combination of the foregoing.

Computer program code for carrying out operations for aspects of the present invention may be written in any combination of one or more programming languages, including an object oriented programming language such as Java, Smalltalk, C++ or the like and conventional procedural programming languages, such as the "C" programming language or similar programming languages. The program code may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider).

Aspects of the present invention are described below with reference to flowchart illustrations and/or block diagrams of methods, apparatus (systems) and computer program products according to embodiments of the invention. It will be understood that each block of the flowchart illustrations and/or block diagrams, and combinations of blocks in the flowchart illustrations and/or block diagrams, can be implemented by computer program instructions. These computer program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks.

These computer program instructions may also be stored in a computer readable medium that can direct a computer, other programmable data processing apparatus, or other devices to function in a particular manner, such that the instructions stored in the computer readable medium produce an article of manufacture including instructions which implement the function/act specified in the flowchart and/or block diagram block or blocks.

The computer program instructions may also be loaded onto a computer, other programmable data processing apparatus, or other devices to cause a series of operational steps to be performed on the computer, other programmable apparatus or other devices to produce a computer implemented process such that the instructions which execute on the computer or other programmable apparatus provide processes for implementing the functions/acts specified in the flowchart and/or block diagram block or blocks.

Input/output or I/O devices (including but not limited to keyboards, displays, pointing devices, etc.) can be coupled to the system either directly or through intervening I/O controllers. Additionally, network adapters also may be coupled to the system to enable the data processing system to become coupled to other data processing systems or remote printers or storage devices through intervening private or public networks. Modems, cable modems, and Ethernet cards are just a few of the currently available types of network adapters.

In the above description, specific details of various embodiments are provided. However, some embodiments may be practiced with less than all of these specific details. In other instances, certain methods, procedures, components, structures, and/or functions are described in no more detail than to enable the various embodiments of the invention, for the sake of brevity and clarity.

The flowchart and block diagrams in the figures illustrate the architecture, functionality, and operation of possible implementations of systems, methods and computer program products according to various embodiments of the present invention. In this regard, each block in the flowchart or block diagrams may represent a module, segment, or portion of code, which comprises one or more executable instructions for implementing the specified logical function(s). It should also be noted that, in some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts, or combinations of special purpose hardware and computer instructions.

Although specific embodiments of the invention have been described and illustrated, the invention is not to be limited to the specific forms or arrangements of parts so described and illustrated. The scope of the invention is to be defined by the claims appended hereto and their equivalents.

What is claimed is:

1. A system for public health data management, the system comprising:
   an input interface to receive input data content descriptive of a public health event;
   a policy data structure implemented on an electronic storage device, wherein the policy data structure is configured to store reporting conditions for a plurality of public health jurisdictions, wherein public health jurisdictions comprise government reporting authorities, and wherein the reporting conditions comprise what data is to be reported, when data is to be reported, and how data is to be reported;
   a notification compliance engine comprising a processor, the notification compliance engine coupled to the policy data structure, wherein the notification compliance engine is configured to review, via the processor, at least some of the reporting conditions of the policy data structure and to identify a relevant reporting condition for the input data content; and
   a data translator coupled to the notification compliance engine, wherein the data translator is configured to derive and arrange output data content based on the input data content according to the relevant reporting condition identified by the notification compliance engine.

2. The system of claim 1, further comprising a data mediator coupled to the input interface, wherein the data mediator is configured to receive the input data content from the input interface and to transform at least some of the input data content to standardized data content compliant with an internal data model of the data mediator.

3. The system of claim 2, further comprising a standardized data repository coupled to the data mediator, wherein the standardized data repository is configured to store the standardized data content.

4. The system of claim 2, wherein the data translator is further coupled to the data mediator, wherein the data translator is further configured to access the standardized data content and generate the output data content based on the standardized data content according to the relevant reporting condition identified by the notification compliance engine.

5. The system of claim 1, wherein the policy data structure is configured to store a content requirement within the reporting conditions, wherein the content requirement specifies data content required by a target public health jurisdiction, and the notification compliance engine is further configured to identify the relevant reporting condition to obtain an indication of the data content required for inclusion in the output data content for the target public health jurisdiction.

6. The system of claim 1, wherein the policy data structure is configured to store a protocol requirement within the reporting conditions, wherein the protocol requirement specifies a data transfer protocol required by a target public health jurisdiction, and the notification compliance engine is further configured to identify the relevant reporting condition to obtain the data transfer protocol for transmission of the output data content to the target public health jurisdiction.

7. The system of claim 1, wherein the policy data structure is configured to store a form within the reporting conditions, wherein the form specifies a plurality of content fields required by a target public health jurisdiction, and the notification compliance engine is further configured to identify the relevant reporting condition to obtain the plurality of content fields for delivery of the output data content to the target public health jurisdiction.

8. The system of claim 1, wherein the policy data structure is configured to store a delivery requirement within the reporting conditions, wherein the delivery requirement specifies a data delivery mechanism required by a target public health jurisdiction, and the notification compliance engine is further configured to identify the relevant reporting condition to obtain the data delivery mechanism for delivery of the output data content to the target public health jurisdiction.

9. The system of claim 8, further comprising a delivery agent coupled to the data translator, wherein the delivery agent is configured to initiate the delivery of the output data content to the target public health jurisdiction according to the data delivery mechanism specified in the delivery requirement of the reporting conditions.

10. The system of claim 1, wherein the input interface is configured to receive the input data content in any of a plurality of data input formats.

11. The system of claim 10, wherein the input interface further comprises a plurality of specialized input interfaces, wherein each specialized input interface is configured to receive the input data content according to a corresponding data transfer protocol.

12. The system of claim 1, further comprising a mailbox coupled to the data translator, wherein the mailbox comprises:
- a mailbox repository to store the output data content for subsequent retrieval by an authorized user; and
- a mailbox interface to facilitate authentication of the authorized user and delivery of the output data content to the authorized user.

13. The system of claim 1, further comprising a feedback interface to provide summary data to a provider of the input data content, wherein the summary data comprises other data identified as potentially relevant to the input data content.

14. The system of claim 1, further comprising a collaborative policy interface coupled to the policy data structure, wherein the collaborative policy interface is configured to receive community submissions of policy modifications, wherein each policy modification is configured to change at least one reporting condition or initiate at least one new reporting condition.

15. The system of claim 1, further comprising a web interface coupled to the input interface, wherein the web interface is configured to provide an online form for entry of the input data content to the input interface.

16. A computer program product comprising a non-transitory computer useable storage medium to store a computer readable program for managing public health data, wherein the computer readable program, when executed on a computer, causes the computer to perform operations comprising:
- receiving input data content descriptive of a public health event;
- generating standardized data content based on at least some of the input data content;
- accessing a policy repository which stores a plurality of reporting conditions for a plurality of public health jurisdictions, wherein public health jurisdictions comprise government reporting authorities, and wherein the reporting conditions comprise what data is to be reported, when data is to be reported, and how data is to be reported;
- identifying a relevant reporting condition for a target public health jurisdiction; and
- generating output data content based on the standardized data content.

17. The computer program product of claim 16, wherein the computer readable program, when executed on the computer, causes the computer to perform further operations comprising:
- storing a content requirement within the reporting conditions, wherein the content requirement specifies data content required by the target public health jurisdiction; and
- identifying the relevant reporting condition to obtain an indication of the data content required for inclusion in the output data content for the target public health jurisdiction.

18. The computer program product of claim 16, wherein the computer readable program, when executed on the computer, causes the computer to perform further operations comprising:
- storing a protocol requirement within the reporting conditions, wherein the protocol requirement specifies a data transfer protocol required by the target public health jurisdiction; and
- identifying the relevant reporting condition to obtain the data transfer protocol for transmission of the output data content to the target public health jurisdiction.

19. The computer program product of claim 16, wherein the computer readable program, when executed on the computer, causes the computer to perform further operations comprising:
- storing a form within the reporting conditions, wherein the form specifies a plurality of content fields required by the target public health jurisdiction; and
- identifying the relevant reporting condition to obtain the plurality of content fields for delivery of the output data content to the target public health jurisdiction.

20. The computer program product of claim 16, wherein the computer readable program, when executed on the computer, causes the computer to perform further operations comprising:
- storing a delivery requirement within the reporting conditions, wherein the delivery requirement specifies a data delivery mechanism required by the target public health jurisdiction;
- identifying the relevant reporting condition to obtain the data delivery mechanism for delivery of the output data content to the target public health jurisdiction; and
- initiating the delivery of the output data content to the target public health jurisdiction according to the data delivery mechanism.

21. The computer program product of claim 16, wherein the computer readable program, when executed on the computer, causes the computer to perform further operations comprising:
- storing the output data content in a mailbox repository for subsequent retrieval by an authorized user;
- authenticating the authorized user in response to a request to retrieve the output data content from the mailbox repository; and
- delivering the output data content to the authorized user in response to successful authentication of the authorized user.

22. The computer program product of claim 16, wherein the computer readable program, when executed on the computer, causes the computer to perform further operations comprising:
- receiving community submissions of policy modifications, wherein each policy modification is configured to change at least one reporting condition or initiate at least one new reporting condition.

23. A method for managing public health data, the method comprising:
- receiving input data content in any of a plurality of data input formats, wherein the input data content is descriptive of a public health event;
- generating standardized data content based on at least some of the input data content;
- accessing a policy repository which stores a plurality of reporting conditions for a plurality of public health jurisdictions, wherein public health jurisdictions comprise government reporting authorities, and wherein the reporting conditions comprise what data is to be reported, when data is to be reported, and how data is to be reported;
- identifying a relevant reporting condition for a target public health jurisdiction; and
- generating output data content based on the standardized data content according to the relevant reporting condition for the target public health jurisdiction.

24. The method of claim 23, further comprising:
identifying a delivery requirement within the reporting conditions, wherein the delivery requirement specifies a data delivery mechanism required by the target public health jurisdiction;
identifying a protocol requirement within the reporting conditions, wherein the protocol requirement specifies a data transfer protocol required by the target public health jurisdiction; and
delivering the output content to the target public health jurisdiction according to the delivery requirement and the protocol requirement for the target public health jurisdiction.

25. The method of claim 23, further comprising:
storing the output data content in a mailbox repository for subsequent retrieval by an authorized user;
authenticating the authorized user in response to a request to retrieve the output data content from the mailbox repository; and
delivering the output data content to the authorized user in response to successful authentication of the authorized user.

* * * * *